United States Patent [19]

Roy, Sr. et al.

[11] Patent Number: 4,902,124
[45] Date of Patent: Feb. 20, 1990

[54] CATARACT MONITORING METHOD AND MEANS

[76] Inventors: Frederick H. Roy, Sr.; Frederick H. Roy, Jr., both of 1800 Arch St., Little Rock, Ark. 72206

[21] Appl. No.: 242,431
[22] Filed: Sep. 6, 1988
[51] Int. Cl.⁴ ............................................. A61B 3/02
[52] U.S. Cl. ................................................. 351/223
[58] Field of Search ......................... 351/223, 205, 233

[56] References Cited

U.S. PATENT DOCUMENTS 3,903,870 9/1975 Berndt .
4,682,867 7/1987 Gould ................................. 351/223

OTHER PUBLICATIONS

Karickhoff, J. R.: Demonstrating the Cataract to the Patient, Am. Intraocular Implant Soc. J., 9: 51–52, 1983.
Chylack, L. T. et al.: Lens Opacities Classification Systems, Arch. Ophthal., 106: 330–334, 1988.

*Primary Examiner*—Rodney B. Bovernick
*Attorney, Agent, or Firm*—Hermann Ivester

[57] ABSTRACT

There is disclosed herein an inexpensive hand-held device to allow a person to monitor the development of his cataract and record it. The device comprises a light source, a diffusion substance and a pinhole.

2 Claims, 1 Drawing Sheet

CATARACT MONITORING METHOD AND MEANS

BACKGROUND OF THE INVENTION

1. Field of the Invention

This invention relates generally to a monitoring method and means for charting the development course of cataracts and other abnormalities in the human eye.

2. Description of the Prior Art

Home devices have become much more popular in the last several years to check for pregnancy, blood pressure, temperature and many other things. Currently, there are no home eye tests to monitor cataracts. Individuals are now more interested in being more involved in their day-to-day health care. However, the prior art is represented by U.S. Pat. No. 3,903,870 issued Sept. 9, 1975 wherein a hand-held device permits a patient to perform a self-examination of the eye and thereby determine if he should seek professional help.

SUMMARY OF THE INVENTION

According to the present invention, a simple and inexpensive methods means is provided for monitoring the development of a cataract after the individual has had a professional make the diagnosis of the existence of a cataract. Thus, the subject matter of the present invention is used after the person has seen a professional who has made an appropriate diagnosis and thereafter, the individual is allowed to monitor the development of the cataract and to make a documentary record with respect thereto. The user then returns to the professional and can render assistance to the professional by showing him the progression that has occurred in the development of the cataract.

More specifically, a light source is energized whereupon the rays of light are collected and transmitted in the form of a beam against a diffusing filter so that the beam is diffused evenly and uniformly over a designated projection plane having a pinhole. The projection plane is then positioned on the visual axis of the user's eye and the pinhole is aligned and location adjusted along the visual axis so that the opacities in the eye are focused as discernible defined shapes.

The user can then trace the outlines of the discernible defined shapes to record the opacities onto a documentary record, thereby permitting both the user and the professional to measure the changes of the opacities from a previously existing condition, thereby to chart the development of the cataract.

DESCRIPTION OF THE PREFERRED EMBODIMENTS

It has been known for hundreds of years that looking at a diffused light source will allow one to view opacities inside the eye. Individuals have viewed their vitreous floaters (moving opacities) by looking at a blue sky, a white wall or a book.

In accordance with the method of the present invention, two types of opacifications can be seen. One is a moving opacity that includes mucus on the front part of the eye and vitreous opacities.

The second type are fixed opacities such as a cataract. If the individual user of the present invention is directed to look at the fixed opacities and to make a line drawing of the outline thereof, he or she is able to accurately represent the discernible outline of what the cataract looks like. By providing the patient or the user with a suitable chart for notation, the person can establish a datum plane on a given date and look with both the right and the left eye and draw what the particular pattern of the fixed opacity is. Then, at a later date, the user or patient can record the appearance of the opacification and by comparing the two separately dated records, the progression or development of the cataract can be measured and determined.

Unlike the prior art, the present invention is not designed or intended to diagnose the presence of a cataract, rather, the present method and apparatus is to assist the user or patient in monitoring the development of the cataract after he has had a professional diagnosis that he is afflicted with such disease.

Figure 1:
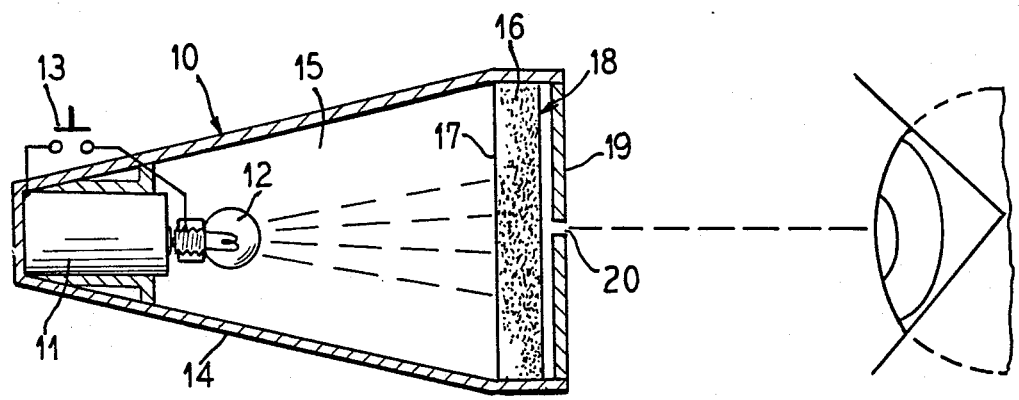
FIG. 1 is a cross-sectional view partly schematic and shows the structure capable of practicing the method of the present invention.
Figure 2:
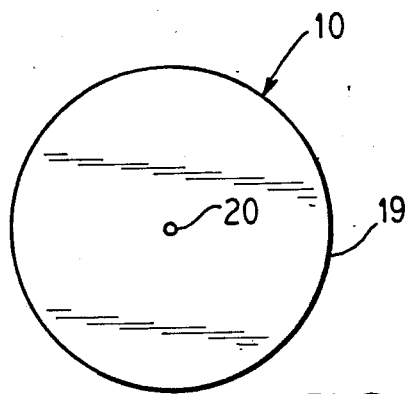
FIG. 2 is an end view of the device showing the pinhole in the end cover.

Referring to FIG. 1, there is shown an apparatus for practicing the method of the present invention. A hand-held device comprising a housing as shown generally at 10 and has an outer shell which is reduced at one end to receive a source of energy such as a dry cell battery 11. A lamp bulb 12, known commercially as reflector lamp bulb #222, is energized by the battery upon closing an appropriate electric circuit controlled by a switch 13 whereupon rays of light from the lamp bulb 12 are emitted and transmitted thereby in the form of a beam. The beam is projected generally longitudinally and axially of the housing 10 which includes a generally cylindrical portion 14 forming a chamber 15 in which is disposed a diffusing filter means 16 and having a back face 17 which intercepts the beam of light thereby to diffuse the beam of light uniformly over a designated projection plane provided by the front face 18 of the diffusion filter means 16.

The front end of the cylinder 14 is closed by a cover 19 which seals the inner chamber on the large end of the filter. The cover is formed with a one-half of a millimeter hole directly in the center of the lens covering.

In use, the device is positioned so that the projection plane is located anteriorly of the user's eye and the diffusing filter. The pinhole 20 is aligned with the visual axis of the user's eye and the location of the pinhole is adjusted along the visual axis to focus the fixed opacities in the eye as discernible defined shapes. Thus, in use, when the device is brought up in front of the user's eye and is positioned so that the user is able to see the light clearly, he is then able to record what he sees of the fixed opacities to chart the actual progress or development of the cataract.

What the user does is to actually trace the outlines of the discernible defined shapes to record the opacities onto a documentary record.

Having made a documentary record, the changes in the size of the opacities from a previously existing position can be charted to establish the rate of development of the opacities.

Although various minor modifications might be suggested by those versed in the art, it should be understood that we wish to embody within the scope of the patent warranted hereon all such modifications as reasonably and properly come within the scope of our contribution to the art.

We claim as our invention:

1. A hand-held opthamological device for monitoring the progression or growth of fixed opacities in the human eye, comprising:
- a generally cylindrical housing disposed on a longitudinal axis and sized to be held in the hand of a user;
- a light source means supported inside one end of said housing and disposed on the central longitudinal axis of said housing, thereby to project a beam of light longitudinally in the direction of said longitudinal axis towards the opposite end of said housing;
- a translucent diffusing filter spaced from said light source means and mounted in said other end of said housing to form a projection plane disposed in perpendicular alignment with said axis for intercepting the longitudinally projected beam of light directly from said light source and diffusing the same uniformly over said projection plane; and
- a base member forming a cover closing said other end of said housing,
  - said cover having a single centered pin hole formed therein and disposed on said central longitudinal axis in alignment with said projection plane;
- whereby a user may manually adjust the pin hole on and along the visual axis of the user's eye so that the opacities in the eye are focused as discernibly defined shapes for monitoring the progression or growth thereof.

2. A hand held device as defined in claim 1, wherein said light source means more particularly comprises:
- a dry cell battery; and
- circuit means connected thereto including a switch on the exterior of said housing in an accessible location, and a light bulb on said axis in the interior of said housing.

* * * * *